(12) United States Patent
He et al.

(10) Patent No.: US 10,098,557 B2
(45) Date of Patent: Oct. 16, 2018

(54) SYSTEM AND METHOD FOR TEMPORAL SPARSE PROMOTING IMAGING OF CARDIAC ACTIVATION

(71) Applicant: REGENTS OF THE UNIVERSITY OF MINNESOTA, St. Paul, MN (US)

(72) Inventors: Bin He, Minneapolis, MN (US); Long Yu, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 15/036,961

(22) PCT Filed: Nov. 17, 2014

(86) PCT No.: PCT/US2014/065933
§ 371 (c)(1),
(2) Date: May 16, 2016

(87) PCT Pub. No.: WO2015/073962
PCT Pub. Date: May 21, 2015

(65) Prior Publication Data
US 2016/0287116 A1    Oct. 6, 2016

Related U.S. Application Data

(60) Provisional application No. 61/905,451, filed on Nov. 18, 2013.

(51) Int. Cl.
*A61B 5/04*    (2006.01)
*A61B 5/00*    (2006.01)
(Continued)

(52) U.S. Cl.
CPC ........ *A61B 5/04012* (2013.01); *A61B 5/0044* (2013.01); *A61B 5/0402* (2013.01);
(Continued)

(58) Field of Classification Search
CPC ... A61B 5/04012; A61B 5/0402; A61B 5/042; A61B 5/0452; A61B 5/055;
(Continued)

(56) References Cited

U.S. PATENT DOCUMENTS 5,414,623 A * 5/1995 Lu .................. G06T 11/006
                                               382/131
6,052,618 A * 4/2000 Dahlke .................. A61B 6/12
                                               600/509

(Continued)

OTHER PUBLICATIONS

Messnarz et al. "A New Spatiotemporal Regularization Approach for Reconstruction of Cardiac Transmembrane Potential Patterns", IEEE Transactions on Biomedical Engineering vol. 51, N. 2, Feb. 2004, pp. 273-281.*

(Continued)

*Primary Examiner* — Carl H Layno
*Assistant Examiner* — Erin M Piateski
(74) *Attorney, Agent, or Firm* — Quarles & Brady LLP

(57) ABSTRACT

A system and method for cardiac activation imaging includes non-invasively or minimally invasively acquiring data about an electrical activation of a heart of a subject using at least one sensor. An activation image of the heart of the subject is reconstructed using a weighted sparse constrained reconstruction.

22 Claims, 12 Drawing Sheets

(51) Int. Cl.
*A61B 6/00* (2006.01)
*A61B 5/055* (2006.01)
*A61B 6/03* (2006.01)
*A61B 5/042* (2006.01)
*A61B 5/0452* (2006.01)
*A61B 5/0402* (2006.01)
*A61B 5/0408* (2006.01)
*G16H 50/50* (2018.01)

(52) U.S. Cl.
CPC ........ *A61B 5/0452* (2013.01); *A61B 5/04085* (2013.01); *A61B 5/055* (2013.01); *A61B 5/7282* (2013.01); *A61B 6/032* (2013.01); *A61B 6/503* (2013.01); *A61B 6/5205* (2013.01); *A61B 5/042* (2013.01); *A61B 5/6852* (2013.01); *A61B 5/742* (2013.01); *A61B 2576/023* (2013.01); *G16H 50/50* (2018.01)

(58) Field of Classification Search
CPC ..... A61B 5/6852; A61B 5/7282; A61B 5/742; A61B 6/032; A61B 6/503; A61B 6/5205; A61B 2576/023; G06F 19/3437
USPC .......... 600/523, 509; 382/131, 232
See application file for complete search history.

(56) References Cited

U.S. PATENT DOCUMENTS 7,646,924 B2   1/2010   Donoho

2010/0310144 A1*  12/2010  Chen .................... G06T 11/006
                                                          382/131
2011/0228999 A1   9/2011   Hsieh
2011/0243419 A1   10/2011  Allmendinger et al.
2012/0008844 A1   1/2012   Bilgin et al.
2012/0197145 A1*  8/2012   Wu ..................... A61B 5/04007
                                                          600/509
2014/0200471 A1*  7/2014   Spector ............. A61B 5/04014
                                                          600/518

OTHER PUBLICATIONS

International Search Report and Written Opinion under dated Feb. 11, 2015 in connection with PCT/US2014/065933.

Fischer, et al., Computationally Efficient Noninvasive Cardiac Activation Time Imaging, Methods of Information in Medicine, 2005, 44(5):674-686.

Liu, et al., Noninvasive Reconstruction of Three-Dimensional Ventricular Activation Sequence From the Inverse Solution of Distributed Equivalent Current Density, IEEE Transactions on Medical Imaging, 2006, 25(10):1307-1318.

Messnarz, et al., A New Spatiotemporal Regularization Approach for Reconstruction of Cardiac Transmembrane Potential Patterns, IEEE Transactions on Biomedical Engineering, 2004, 51(2):273-281.

European Patent Office, Extended European Search Report, Application No. 14862981, dated Aug. 14, 2017.

* cited by examiner

SYSTEM AND METHOD FOR TEMPORAL SPARSE PROMOTING IMAGING OF CARDIAC ACTIVATION

CROSS-REFERENCE TO RELATED APPLICATIONS

This application is a 371 application of PCT/US2014/065933 filed Nov. 17, 2014 which claims priority to U.S. Provisional Application Ser. No. 61/905,451, filed Nov. 18, 2013, both of which are incorporated herein by reference for all purposes.

STATEMENT REGARDING FEDERALLY SPONSORED RESEARCH

This invention was made with government support under HL080093-01A2 awarded by the National Institutes of Heath. The government has certain rights in the invention.

BACKGROUND

The present disclosure relates to systems and methods for acquiring medical data and, more particularly, to imaging of cardiac activation.

Cardiac disease is a significant challenge to public health and a leading killer in the United States, costing more than 270 billion dollars annually in the United States alone. Each year, about 400,000 sudden cardiac deaths are reported in the United States while a major portion of them are induced by ventricular arrhythmias. In clinical practice, anti-arrhythmic medications are usually administered to suppress the life-threatening syndromes. For the medically refractory cases, catheter ablation has become a standard procedure to eliminate the arrhythmias. The success of such catheter ablation relies on information regarding the arrhythmogenesis. Contact and non-contact intra-cardiac mapping technologies have been employed to guide catheter ablative procedures. However, limited by its invasive nature, these approaches are often time consuming and can only map the cardiac electrical activity on the endocardium of a single or only partial ventricular chamber. Therefore, there is a clinical need to develop non-invasive imaging modalities that can image the cardiac electrical activity throughout the 3D myocardial volume. Such clinical information will improve the effectiveness and efficiency of catheter ablation treatment and also help elucidate the mechanisms of ventricular arrhythmias.

Efforts have been made pursuing noninvasive approaches of mapping cardiac electrical activity by solving the inverse problem of electrocardiography (ECG). Moving dipole localization techniques seek to represent whole heart electrical activity with either one or several moving dipoles. Epicardial imaging techniques expand the solution space from few dipole sources to potential distributions over the epicardial surface. Heart surface activation imaging, alternatively, directly solves myocardial activation time on the heart surfaces based on a physiological model. These methods have been shown to provide potentially valuable information noninvasively, although they estimate cardiac electrical activity over the epicardium or the heart surfaces (including epicardial and endocardial surfaces) instead of over the 3D myocardium.

Over the past decade, cardiac electrical imaging approaches considering the whole myocardium have been pursued. Physiological model based methods incorporate a priori knowledge based physiological model into inverse solutions to solve the ECG inverse problem. Recently, a physical-model based 3D Cardiac Electrical Imaging (3DCEI) approach has been developed and validated on various animal models, such as rabbits and canines, in which good concordance was observed with 3D intra-cardiac mapping results. However, the minimum energy based Weighted Minimum Norm (WMN) method employed by 3DCEI limits the spatial-temporal resolution and robustness against non-Gaussian disturbance such as geometrical modeling error and electrode registration error, which can be introduced in realistic scenarios due to limited raw data quality. The electrophysiology-irrelevant minimum energy constraints imposed may become dominant in reconstruction, leading to a smoothed and distorted imaged activation sequence.

Therefore, the need remains for new and improved non-invasive imaging modalities that can image the cardiac electrical activity throughout the 3D myocardial volume.

Similarly, efforts have been pursued for minimally invasive cardiac imaging using recordings made by catheter. However, there is a need to improve catheter based activation imaging throughout the 3D myocardial volume.

In parallel to electrocardiographic imaging, efforts have also been made to image cardiac electrical activity from magnetocardiographic recordings made out of torso. However, high resolution activation imaging from magnetocardiography (MCG) has been challenging.

SUMMARY

The present invention overcomes the aforementioned drawbacks by providing systems and methods for cardiac electrical sparse imaging (CESI), which is a new electrical imaging technique. CESI provides a 4D inverse problem formulation to incorporate sparse property of cardiac electrical activity to preserve the temporal resolution and detailed activation information for improved imaging accuracy and robustness in comparison with traditional linear inverse solutions. CESI reconstructs cardiac electrical activation in a weighted group sparse promoting strategy based on a physical model to exploit sparse properties of electrical activity and, therefore, improve the spatial-temporal resolution and the robustness in imaging the cardiac activity.

In accordance with one aspect of the invention, a system is disclosed for cardiac activation imaging. The system includes at least one data acquisition device configured to acquire data about an electrical activation of a heart of a subject and a processor. The processor is configured to receive the data acquired by the at least one data acquisition device and generate a cardiac electrical activation image by reconstructing an activation image of the heart of the subject using a weighted sparse constrained reconstruction.

In accordance with another aspect of the invention, a method is disclosed for acquisition of cardiac activation imaging data. The method includes acquiring data about an electrical activation of a heart of a subject using at least one sensor and reconstructing an activation image of the heart of the subject using a weighted sparse constrained reconstruction. The method also includes displaying the activation image of the heart.

In accordance with another aspect of the invention, a system is disclosed for minimally invasive imaging of cardiac activation from data collected by a catheter. The system includes acquire electrophysiological data simultaneously or sequentially from a catheter, and anatomic information, and reconstruct an activation image of the heart of the subject using a weighted sparse constrainted reconstruction, and display together with cardiac anatomy or catheter mapping results.

In accordance with another aspect of the invention, a system is disclosed for non-invasive imaging of cardiac activation from data collected by a MCG recording device. The system includes acquire MCG data, and anatomic information, and reconstruct an activation image of the heart of the subject using a weighted sparse constrainted reconstruction, and display together with cardiac anatomy or other cardiac mapping results.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Non-invasive approaches to image cardiac activation can provide important information besides the traditional intra-cardiac mapping to aid ablation therapy and cardiovascular research. The present invention provides a system and method for cardiac electrical sparse imaging (CESI). CESI can image the cardiac electrical activation throughout the myocardium, preserving full temporal resolution and at high spatial resolution. As will be described, CESI can employ a 4D inverse problem formulation to incorporate sparse property of cardiac electrical activity to preserve the temporal resolution and detailed activation information for improved imaging accuracy and robustness in comparison with traditional linear inverse solutions. CESI reconstructs cardiac electrical activation in a weighted group sparse promoting strategy based on a physical model to exploit sparse properties of electrical activity on myocardium and, therefore, improve the spatial-temporal resolution and the robustness in imaging the cardiac electrical activity three dimensionally. As will be described, the imaged results were validated by simultaneous intra-cardiac transmural recording and compared with those from traditional 3D imaging approaches represented by weighted minimum norm (WMN) method as partial evaluation.

Figure 1:
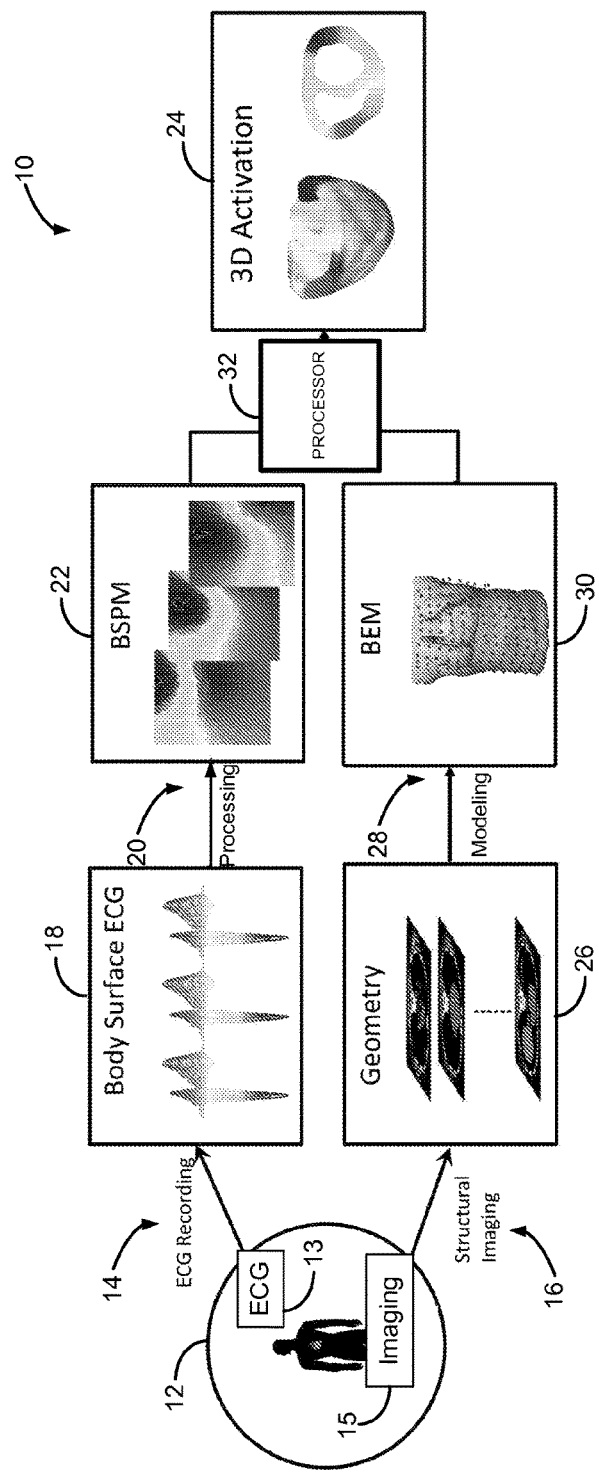
FIG. 1 is a schematic illustration of a system in accordance with the present invention.

In particular, referring to FIG. 1, a system in accordance with the present invention is illustrated. The system 10 includes at least one system to acquire information from a patient 12. For example, an ECG system 13 having at least one electrode or sensor may be configured to be placed on an external surface of the patient 12 to provide ECG recordings 14. Also, a medical imaging system 15 may be employed to acquire medical imaging data from the patient 12 to generate structural or anatomical imaging data. The ECG recordings 14 can be used to generate body surface ECG reports 18. The body surface ECG reports 18 can be processed further to generate a body surface potential map (BSPM) 20. As will be described, the recorded ECG data 14, regardless of the particular electrode or sensor design or configuration used for acquisition, can be transformed to BSPMs and, used to create CESI activation images 24, which may be activation images of the heart of the patient 12 reconstructed using a weighted sparse constrained reconstruction.

To do so, the structural imaging data 16 is used to create 3D or a series of 2D image slices that contain information about the geometry or underlying anatomy information 26 of the patient 12. To this end, the medical imaging system may include a computed tomography (CT) imaging system, a magnetic resonance imaging (MRI) system, or a variety of other imaging modalities capable of providing geometric information about the anatomy of the patient 12. The geometry or underlying anatomy information 26 is used in a modeling process 28 to generate a geometric model of the subject 12 that describes the patient's anatomy using boundary element method (BEM) 30. This geometric model is combined with the data from the BSPMs 22, using a processor 32 to implement a sparse reconstruction process that will be described, to generate the 3D activation images 24. As will be further described, the above-described processing 20 and modeling 28 may also be performed in the processor 32, or may be performed using other processors.

As will be described, inverse solutions have been investigated for cardiac electrical imaging, such as using equivalent current density (ECD) models. However, these investigations did not incorporate any physiological knowledge and reconstruct each timeframe independently, leading to a temporal smoothing effect and losing temporal resolution and details. As will be described, sparse constraints can be applied to inverse problem formulation in order to produce solutions with sparse features. However, simple sparse constraints are sensitive to noise and struggle to present the temporal dynamics properly. The CESI methods described herein, provide dipole-wise temporal weighted sparse reconstructing strategy that can be implemented by a processor to create the CESI activation images 24.

Trans-Membrane Potentials (TMPs) and Temporal Sparse Property in Spatial Derivative When a myocardial cell is activated, the TMP has a transient rise from the −90 mV resting state to the plateau potential at around 0 mV. Regardless of individual variations in the resting or plateau potential, the impulse of trans-membrane current flow, corresponding to the temporal derivative of TMP, can indicate the time of cell activation by sharp peaks while during the remainder of the cardiac cycle, the cell is nearly electrically silent. In accordance with the present invention, this can be reviewed as a sparse property of the cardiac electrical activity in the temporal domain that can potentially be exploited for enhancement in imaging.

Figure 2A:
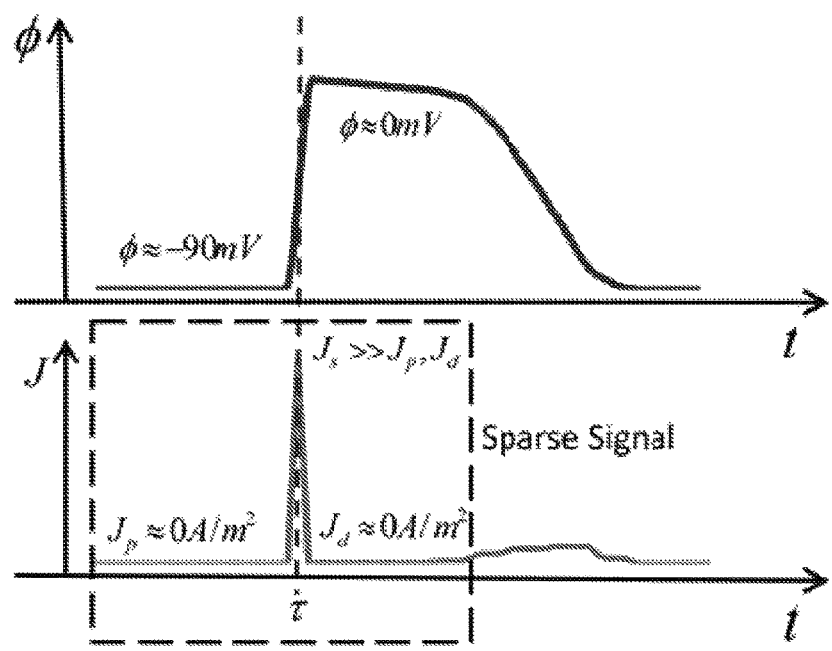
FIG. 2A is a graph showing transmural electricity.
Figure 2B:
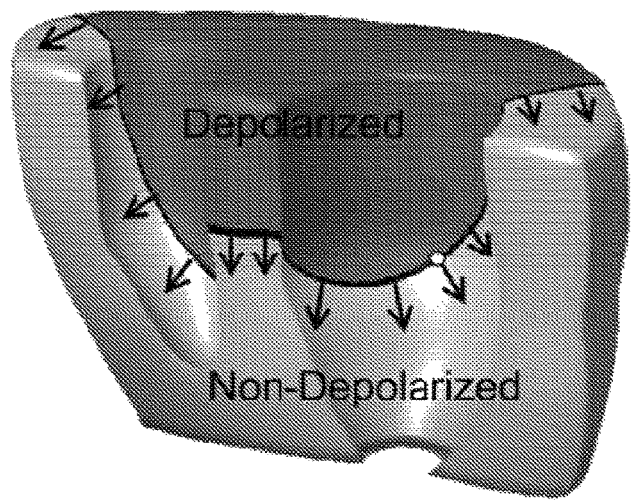
FIG. 2B is an illustration of a depolarization state at an instant, τ.

The spatial derivative of the TMP, equivalently, can be an indicator of activation propagation throughout the spatial domain of the myocardium. Activation propagates through the heart and generates a wave front between the resting and the depolarized myocardial tissue. For each myocardial cell, the TMP time course consists of two distinguished phases and a rapid transition between them. For example, FIG. 2A is a graph showing transmural electricity and FIG. 2B is an illustration of a depolarization state at an instant, $\tau$. Thus, together FIGS. 2A and 2B illustrate the temporal sparse property of cardiac electrical activity. The rapid potential shift from the polarized −90 mV to the depolarized 0 mV during propagation can generate an excitation wave front as well as a spike in current density for the myocardium at the wave front. On the other hand, the current density during the relatively stable potential in both resting and plateau stage is much smaller and can be considered as electrically silent compared with the spike. Therefore, the current density in each site of the myocardium can be assumed as a sparse signal. However, this sparsity can only hold in the temporal domain. Although each myocardial cell in a cardiac cycle is activated only once, a considerably large portion of the heart can possibly be excited at the same time as excitation propagates. Note that the spatial derivative of TMP along a certain direction can be directly measured by bipolar recordings, a well-established mapping technology. As will be described, this realization allowed validation of the performance of the cardiac electrical imaging results in a rigorous manner.

Equivalent Current Density (ECD) Model & Transfer Function

At location r and time instant t, equivalent current density $J_{eq}$ can be defined as:

$$J_{eq}(r,t) = -G_i(r)\nabla\Phi_m(r,t) \quad (1);$$

where $G_i(r)$ stands for the intracellular effective conductivity tensor at location r and $\Phi_m(r,t)$ is the transmembrane potential.

Based on bidomain theory and distributed ECD model, the discrete architecture of the myocardial cell can be generalized into a model on a macroscopic continuum where the electrical activity in myocardium can be represented with two components: intracellular and extracellular domains divided by a theoretical membrane. The electrical behavior of assumed quasi-static state electrical field is governed by:

$$\nabla \cdot [(G_i(r)+G_e(r))\nabla\Phi_n(r,t)] = \nabla \cdot \vec{J}_{eq}(r,t) \quad (2);$$

where $G_e(r)$ and $G_i(r)$ are the intracellular and extracellular effective conductivity tensors and $\Phi_e(r,t)$ is the extracellular potential at location r, time instant t. The differential equation (2), with boundary element model approximation, can be linearized into a matrix-vector transfer function shown as:

$$\vec{\Phi} = L\vec{J} \quad (3);$$

where L stands for the transfer matrix $\vec{\Phi}$, $\vec{J}$ are vectors of body surface potentials and equivalent current density at the source grid points inside the myocardium, respectively. Matrix L is an M×3N matrix connecting M sensor measurements and the current density dipole momentums on N myocardial grid points. On each grid point, 3 momentums are considered in equivalence of a current density vector. Equation (3) represents a linear relation between body surface ECG and equivalent current density over a number of grid points covering the myocardium at a certain time instant. To expand this to the entire time course, equation (3) can be reformed into:

$$\vec{\Phi}_T = L_T \vec{J}_T \quad (4)$$

$$L_T = \begin{bmatrix} L & & & \\ & L & & \\ & & \ddots & \\ & & & L \end{bmatrix} \quad (5)$$

where $L_T$ is a MT×3NT matrix which connects the body surface potentials over a period of time, $\Phi_T$, and the equivalent current density over a period of time $J_T$. In equation (4), a transfer function from the electrical activity on a time course for each myocardial voxel to body surface potential for the time window is constructed. The temporal dynamic of cardiac electrical activity and its sparse property can be described in $J_T$ and shown in the reconstructed solutions provided hereafter.

The matrix-vector equation (3) can be represented as the following when MCG data is involved:

$$B = AJ \quad (3b)$$

where A stands for the transfer matrix relating cardiac sources J to magnetic field B; and B,J are vectors of magnetic field produced by cardiac currents out of the torso, and equivalent current density at the source grid points inside the myocardium, respectively. Matrix A is an M×3N matrix connecting M sensor measurements and the current density dipole momentums on N myocardial grid points. On each grid point, 3 momentums are considered in equivalence of a current density vector. Equation (3b) represents a linear relation between MCG and equivalent current density over a number of grid points covering the myocardium at a certain time instant. To expand this to the entire time course, equation (3b) can be reformed into:

$$B_T = A_T J_T \quad (4b)$$

Where $A_T$ is similar to (5) except $L_T$ refers to transfer function for electric potential and $A_T$ refers to transfer function for magnetic field.

Weighted Sparse Constrained Reconstruction

As presented above, equation (4) formulates a forward problem that connects the spatiotemporal dynamics of cardiac electrical activity with the body surface potential maps (BSPMs). However, the formulated problem is seriously ill-posed and cannot be solved directly. Minimum energy based inverse solutions have been investigated for cardiac electrical imaging. However, the pure physical constraints fail to incorporate any physiological knowledge and reconstruct each timeframe independently, leading to a smoothing effect that decreases temporal resolution and distorts the activation sequence. Sparse constraints can be applied to the inverse problem formulation in order to produce solutions with sparse features. However, simple sparse constraints are sensitive to noise and cannot present the temporal dynamics in the heart properly. The present CESI method provides a dipole-wise temporal weighted sparse reconstructing strategy will be applied as:

$$\hat{J}_T = \operatorname{argmin}\left(\left\|\vec{J}_T - L_T \vec{\Phi}_T\right\|_2^2\right); \quad (6)$$

$$s.j. \sum_t^T W_{t,i} \|\vec{J}_{t,i}\|_2^1 < \mu E_i \text{ for all } i; \quad (7)$$

where $W_{t,i}$ represents the soft temporal weights of time instant t at location grid point i. $\vec{J}_{t,i}$ stands for the current density vector $[J_x, J_y, J_z]$ at instant t and myocardial source grid i. $E_i$ represents the estimated energy of ECD along time course t at location i. $W_{t,i}$ and $E_i$ can be derived by:

$$W_{i,t} = \exp(-C_{t,i}/C_{max}); \quad (8)$$

$$E_i = \sqrt{\sum_T C_{t,i}^2}; \quad (9)$$

$$J_w = \operatorname{argmin}\|LJ_w - \Phi\|_2^2 + \|W_w J_w\|_2^2; \quad (10)$$

where $C_{t,i}$, is the amplitude of WMN reconstructed current density $J_w$ at instant t and myocardial source grid i solved with weighted minimum norm method as described in Z. Liu, C. Liu and B. He, "Noninvasive Reconstruction of Three-Dimensional Ventricular Activation Sequence form the Inverse Solution of Distributed Equivalent Current Density," IEEE Transaction Medical Imaging, vol. 25, pp. 1307-1318, 2006, which is incorporated herein by reference in its entirety. $C_{max}$, is the maximum value of $C_{i,t}$ along the time course T at each location i. $W_{t,i}$ is designated to help stabilize the sparse solutions at the same time evading the smearing effect and distortion a minimum norm solution may have. When $C_{t,i}$ gets smaller, indicating a smaller likelihood that the activation may occur, $W_{t,i}$ becomes larger, imposing a larger penalty and the final electrical spikes are less likely to be occur at the instant.

All the current density time course from equation (10) may be normalized so that the total penalty on each site will be approximately same. Therefore, the balanced of each grid point can be kept. The constraints in equation (7) have a soft guiding effect on the final temporal sparse results. When the weighted minimum norm is "confident" about the reconstructed result, namely a distinguished peak is reconstructed, the penalty for disagreeing will be larger. On the other hand, in the situation where only smoothed waveform or multiple peaks are generated due to noisy background or modeling error, which is the major source of error in WMN method, CESI will seek for activation in a larger range and rely more on the information from BSPM and other "confident" results. In this way, the merit of WMN can be preserved while the weakness can be avoided. E, on the opposite side of the constraints, is directly linked to the energy of the weighted minimum norm solutions and the effect of distributing lead-field energy can be canceled out.

Note that equation (6) serves as the dominating term in reconstruction while equation (8) only bring in minimum norm inverse solutions as secondary guiding information. In contrast to the minimum energy based constraints from which most entries in the solution vector can be non-zero to compensate the residual term in equation (6), the sparse constraints in equation (7) designed in the present method enforce electrical silence except for the very instant of activation. Therefore, the tendency for loss of temporal resolution and distortion is heavily penalized by the residual term due to the total absence of electrical activity in other instants and the information from BSPM can be efficiently reflected in the reconstructed results without compromise to a stronger regularization term as the disturbance from noise or modeling error become more serious. At the same time, the sensitivity of sparse reconstruction to sensor noise can be overcome by weighting based on the Gaussian-noise-robust minimum energy solutions. Instead of a direct L1, the sparse constraints in equation (7) adapt a grouped sparse formulation in which the three momentums in $\vec{J}_{t,i}$ are considered grouped and only the amplitude of $\vec{J}_{t,i}$ is sparse and only in the temporal domain. The $\mu$ in equation (7) can be determined by a data driven regularization algorithm such as the L-curve method. Equations (6) to (9) define a convex constrained problem and can be solved equivalently using various methods. As a non-limiting example, these can be solved with CVX, a software package for specifying and solving convex programs. Activation time, according to the peak criterion, may be computed based on CESI imaged electrical activity and the 3D activation sequence throughout the myocardium is generated accordingly.

CESI, with its novel formulation, stressing sparsity in the temporal domain, incorporates the whole 4D spatiotemporal cardiac dynamics in reconstruction. The temporal dynamic specific sparse formulation is applied in the imaging of a 4D functional process allowing sparse and non-sparse properties to cooperate in imaging for a higher accuracy and spatiotemporal resolution. The method does not promote sparsity in spatial domain but only in temporal domain. Thus, the imaging result of the present method can better image the spatial cardiac activation in a spatial sparse or non-sparse manner. Due to the temporal sparse constraints, the spatial area of electrical activation at a specific instant is mainly determined by the information from the residual term in equation (6). In contrast, as will be demonstrated, the minimum norm method can only generate a smoothed waveform along the time course and large of the myocardium will be electrically active during most of the beat. Therefore, the effective spatial resolution of CESI is improved even with the same source grid resolution by avoiding spatial smoothing effects. This property in spatiotemporal domain improves the method's compatibility and performance for both the early phase, where the activation is sparse, and the later phase, where a major portion of the myocardium is in activation, of the cardiac cycle.

For MCG activation imaging, equation (4b) instead of (4) should be used and the CESI algorithm can be applied to MCG data.

Computer Simulation

In order to evaluate the performance of the described method on human applications in a realistic scenario, a cellular automaton heart model embedded in a realistic heart-torso volume conductor model was used. A generalized cardiac anisotropy was incorporated into the heart model and the myocardial fiber rotated counterclockwise over 120 degrees from the outermost layer to the innermost layer. The conduction velocity is 0.8 m/s along the fiber and 0.3 m/s transverse. The myocardium consists of a total of 30,085 cardiac automatons and 4,096 torso surface vertices were constructed. Two hundred electrodes were evenly distributed on both the chest and the back in the computer simulation. Pacing simulations on various locations were employed, including the basal anterior (BA), basal left wall (BLW), basal right wall (BRW), basal posterior (BP), basal Septum (BS), middle left wall (MLW), middle right wall (MRW), middle anterior (MA), mid-septum (MS), middle posterior (MP), apical anterior (AA) and Apical posterior (AP). Dual site pacing was also simulated in the present study with seven pairs of pacing sites selected throughout the ventricle myocardium. One pacing site was fixed at the mid lateral RV free wall while the other one gradually moved towards the mid left wall. BSPMs were computed by means of the Boundary Element Method (BEM) with simulated cardiac electrical sources using the cellular automaton model.

Various kinds of experimental noise and modeling error were considered to simulate noise-contaminated measurements in a clinical setting. White Gaussian noise of different levels (20-80 µV) was utilized as the sensor noise. Noise signal that randomly selected from hospital ECG recordings with ECG waveform rejected was also used to simulate realistic noise such as power line interference, medical device interference and movement drift. Heart and torso modeling error were also simulated where the size of the torso was inflated by 10% and the location of the heart inside was moved 4 mm towards the lung. To simulate the electrode localization errors that could occur in the realistic applications, such as electrode-CT geometrical co-registration, the electrodes were moved 1 cm upward from its original locations.

Validation in Animal Experiments

Figure 3:
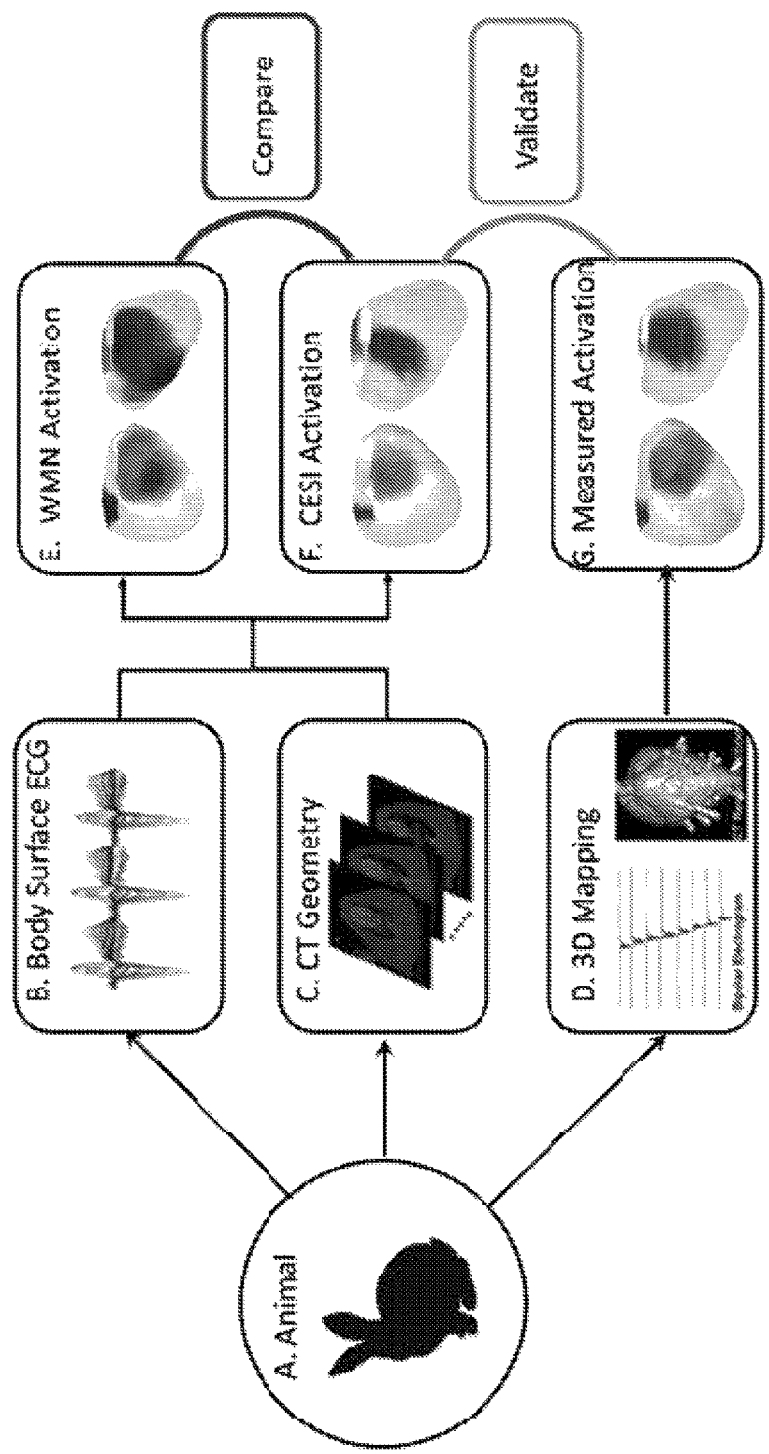
FIG. 3 illustrates an experimental paradigm of animal experiment, where A shows an experimental animal, B shows a multi-channel body surface ECG, C shows geometrical information from CT scan, D shows a intra-cardiac transmural recording simultaneously done with body surface ECG collection, E shows an activation sequence imaged with WMN method, F shows an activation sequence from the CESI method, and G shows a measured activation sequence from intra-cardiac transmural recording.

To validate the described imaging method, experimental data was collected in two healthy New Zealand rabbits. In particular, FIG. 3 illustrates the experimental setup. In brief, cardiac CT and torso CT were performed on the experimental rabbits prior to in vivo mapping. About 60 BSPM electrodes were uniformly placed covering the anterior and lateral rabbit. Approximately, 20-25 transmural needles were inserted in the left and right ventricles of the rabbit after median sternotomy with each needle carrying 8 bipolar sensors 500 µm distant to each other. The chest and skin were carefully closed after needle insertion. Bipolar electrograms were recorded from all electrodes continuously and simultaneously with body surface ECG mapping. After the recording, electrode needles were replaced with metallic label. CT scans were performed on the excised and fixed hearts to obtain precise 3D localization of the transmural electrodes. A Gaussian interpolation was performed on the activation time detected from intra-cardiac bipolar recording according to the CT geometry to generate a 3D measured activation map. The rabbit myocardium was tessellated into around 10,000 grid points evenly located within the 3D ventricular myocardium. There were around 160-200 intra-cardiac bipolar electrodes placed in both the ventricles for intra-cardiac mapping. The ventricular activation sequences were imaged from the BSPM and quantitatively compared with those recorded simultaneously.

Data Analysis

Correlation Coefficient (CC), Relative Error (RE), Localization Error (LE) and Relative Temporal Shrinkage (RTS) were computed for both computer simulation and animal experimental data, as defined below:

$$CC = \frac{\sum_i (AT_i - MT_i) \cdot (ATA_i - MT_i)}{\sqrt{\sum_i (AT_i - MT_i)^2} \cdot \sqrt{\sum_i (ATA_i - MT_i)^2}};$$

$$RE = \sqrt{\frac{\sum_i (AT_i - MT_i)^2}{\sum_i MT_i^2}};$$

$$RTS = \frac{T_s - T_I}{T_s};$$

where $AT_i$ is the activation time of grid point i in the imaged activation sequence whereas $MT_i$ is the measured activation time at the identical position from the measured activation map. $T_s$ is the simulated or measured total activation time and $T_I$ is the Imaged activation total time. Localization Error is defined as the spatial distance between the imaged activation initiation and the pacing site in simulation and animal study.

The Weighted Minimum Norm (WMN) method has been used in the previous 3D cardiac electric imaging studies and has shown to have a generally good performance in imaging accuracy among the minimum norm based methods. Therefore, the performance of the CESI method was evaluated as compared with the WMN method. In all computer simulation and animal experiments, both CESI and WMN methods were performed independently and the results from both of the approaches were compared.

Results

A. Computer Simulations

Figure 4:
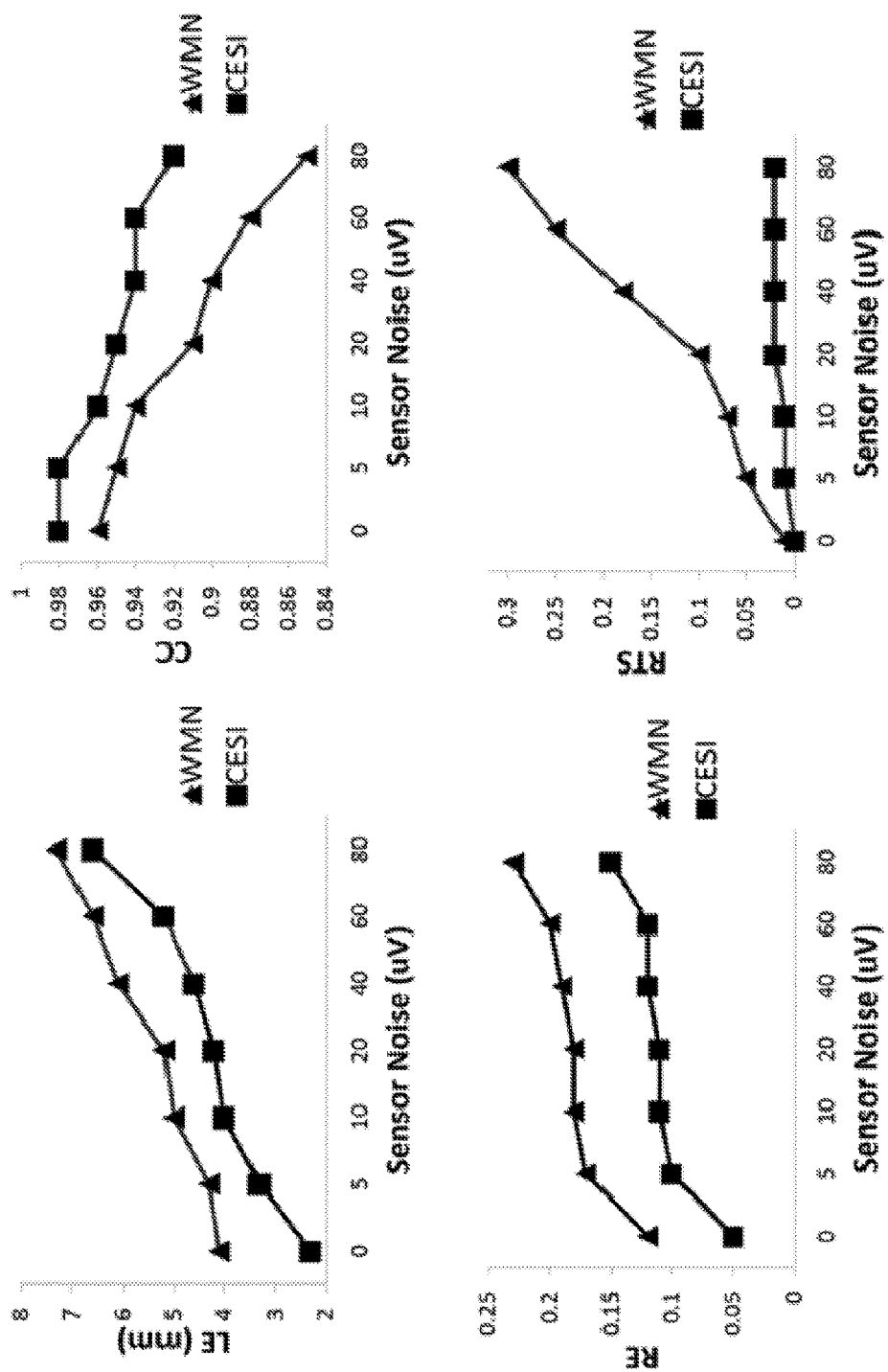
FIG. 4 is a set of graphs showing a comparison of imaging statistics between the CESI method and the WMN method for 12 site single pacing simulations.

Twelve different pacing sites were used in the single pacing paradigm. For each pacing site, various levels of Gaussian white noise were added to the computed BSPM to simulate noise-contaminated measurements. The statistics of averaged CC, RE, LE and RTS on 12 pacing sites are summarized in FIG. 4 to show the averaged statistics of LE (top left), CC (top right), RE (bottom left), and RTS (bottom right). Also, Table 1 provides, as follows:

|  | WMN | CESI |
| --- | --- | --- |
| CC | 0.83 ± 0.05 | 0.91 ± 0.03 |
| RE | 0.26 ± 0.05 | 0.15 ± 0.02 |
| LE (mm) | 7 ± 1.4 | 4 ± 1.4 |
| RTS | 0.21 ± 0.08 | 0.02 ± 0.004 |

The standard deviations of Gaussian white noise added to the BSPMs were 0, 5 10, 20, 40, 60, 80 µV, respectively. Results in FIG. 4 and Table 1 show that CESI has demonstrated a general improvement over WMN in all four statistics. The imaging accuracy such as CC, RE and LE degrades slower than WMN while the noise level goes up and CESI can still maintain CCs as high as 0.92 and 0.94 even under the noise level as high as 60 and 80 µV. As for RTS, CESI was barely affected by the noise and maintains the temporal resolution under each of the noisy circumstances. Dual site pacing simulations were also performed to evaluate the CESI method and the statistics are summarized in Table 2, as follows:

|  | 20 µV Gaussian White Noise | | Hospital Recorded Noise | |
|---|---|---|---|---|
|  | WMN | CESI | WMN | CESI |
| CC | 0.85 ± 0.08 | 0.89 ± 0.07 | 0.80 ± 0.07 | 0.89 ± 0.07 |
| RE | 0.25 ± 0.06 | 0.12 ± 0.06 | 0.30 ± 0.05 | 0.14 ± 0.08 |
| LE (mm) | 4.2 ± 2.1 | 3.9 ± 2.0 | 5.6 ± 3.2 | 4.1 ± 1.7 |
| RTS | 0.2 ± 0.03 | 0.02 ± 0.004 | 0.25 ± 0.06 | 0.02 ± 0.005 |

Figure 5A:
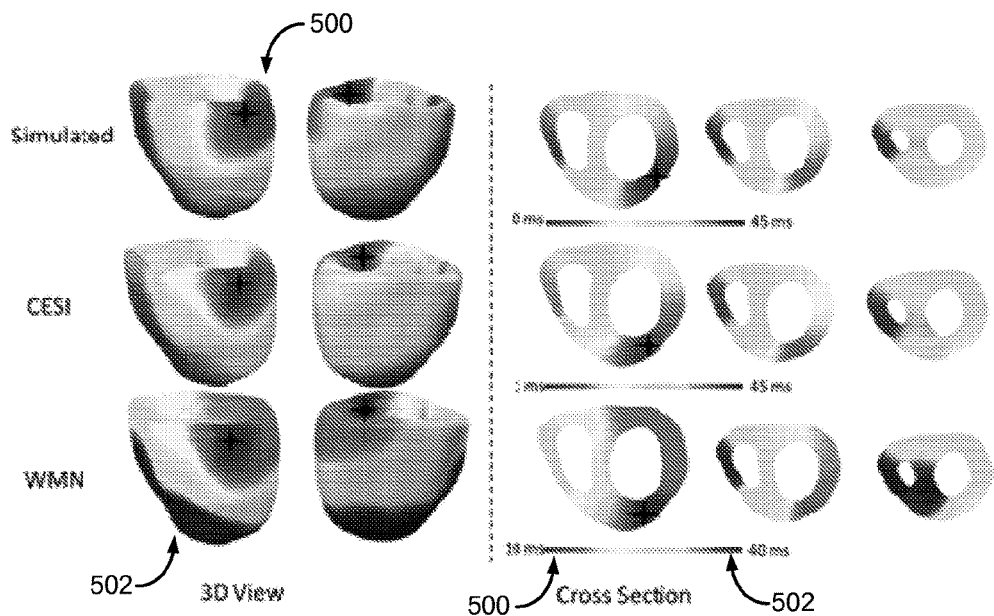
FIGS. 5A through 5D provide sets of images that compare between a simulated activation sequence and an imaged activation sequence from the CESI method and the WMN method.
Figure 5B:
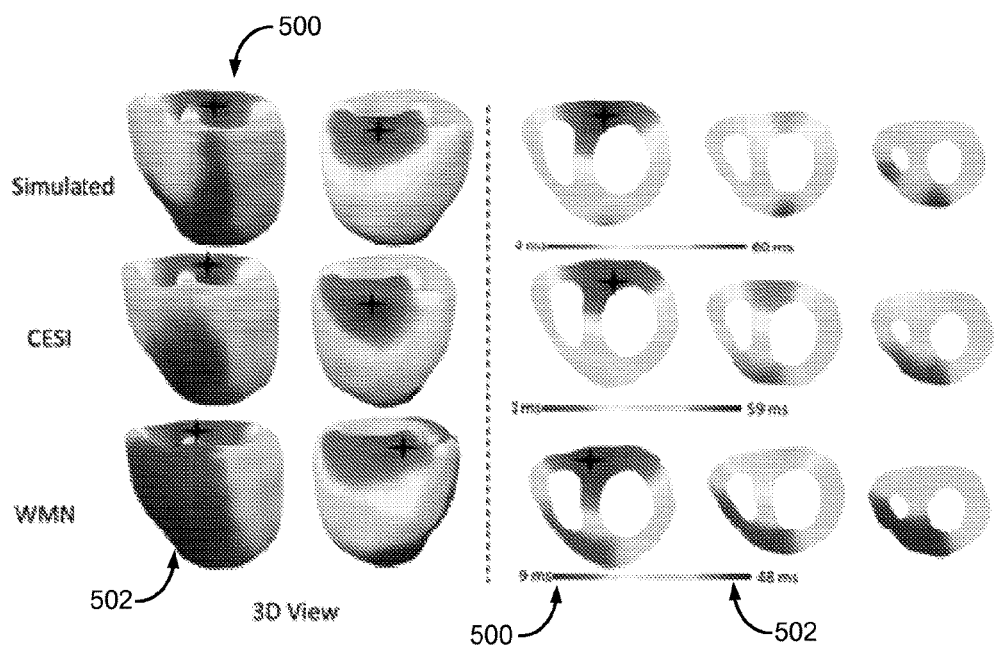
Figure 5C:
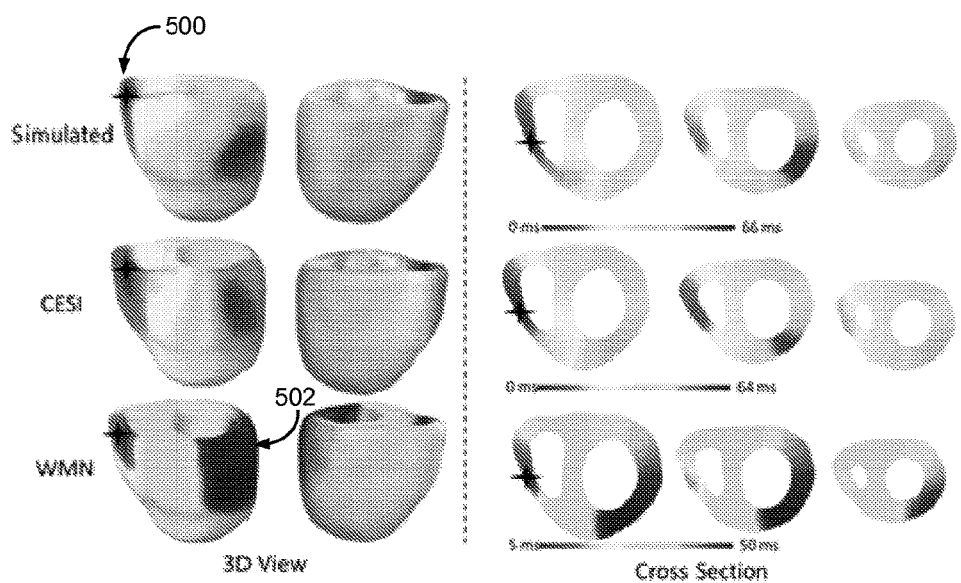
Figure 5D:
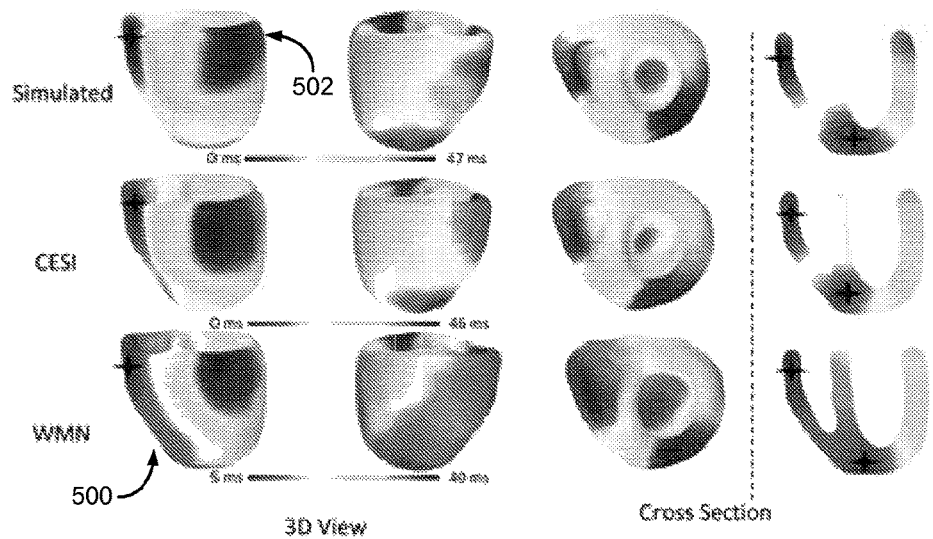

Also, FIGS. 5A-5D present examples of single and dual site pacing computer simulation. All figures are color coded from early activation 500 to late activation 502. For each activation sequence, the color code is adapted to the length of the activation and marked in the color bar. Simulated activation sequences are presented in the first row of each panel in the figure. The generated BSPMs were contaminated with realistic noise recorded from the hospital setting filtered with a 1-30 Hz band pass FIR filter. The results from both approaches (CESI and WMN) are shown in the middle and the bottom row in each panel. FIGS. 5A-5C show single site pacing simulations on the LV basal anterior wall (FIG. 5A), basal posterior wall (FIG. 5B), and RV free wall (FIG. 5C), while FIG. 5D shows an example of dual site pacing simulation on the RV free wall and apical septum. CESI imaged activation sequences only showed a minimal loss of temporal resolution (~1 ms) and demonstrated better accuracy on the general propagation pattern, in comparison to the delay of WMN estimated initial activation. For single pacing sites, CESI results demonstrated higher concordance to the simulated results and suffered less of a blurring effect compared with the WMN results. The blurring effect shown in the WMN solutions in the figures is most significant at the earliest and the latest period of activation, indicating a non-linear distortion on imaged activation time which can be observed to be much relieved in CESI results. It can be seen from FIGS. 5A-5D that CESI can image the early activation region clearly and the initiation is shown to be in good agreement with the simulated activation pattern. The propagation pathway is also well depicted both on the myocardial walls, close to epicardial surface, and the deep region inside the heart along the septum. The termination of the beat was also localized correctly, only with minor differences in the late activation pattern. In FIG. 5D, the dual site pacing simulation, the contrast of CESI imaged activation to distinguish two pacing sites is significantly higher than WMN results. The two pacing sites can be clearly identified from the CESI imaged results and the propagation pattern is in better agreement with the simulated pattern than WMN results. The activation pattern in the myocardium around the two pacing sites is better imaged as a result of temporal resolution preservation. Both the pacing sites were imaged to be initiated independently at 0 ms, at the very beginning of the beat without interfering each other regardless of their differences in location. The activation pattern between the pacing sites is also well imaged whereas that in WMN result is smeared due to the loss of temporal resolution. The statistics of simulation results with hospital recorded noise are summarized in Table 1 (single site pacing) and Table 2 (dual site pacing).

Figure 6A:
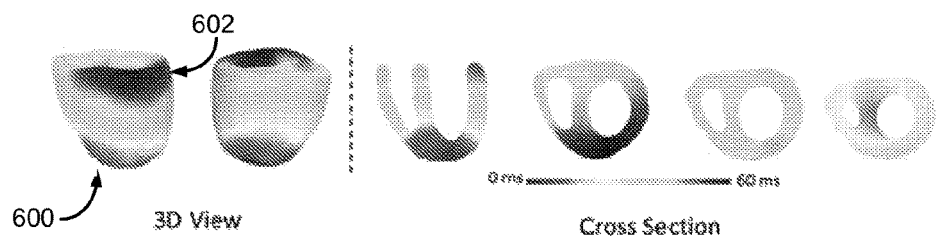
FIGS. 6A-6E provide sets of images that compare imaged results from the CESI method and the WMN method studies from pacing simulation with various modeling errors.
Figure 6B:
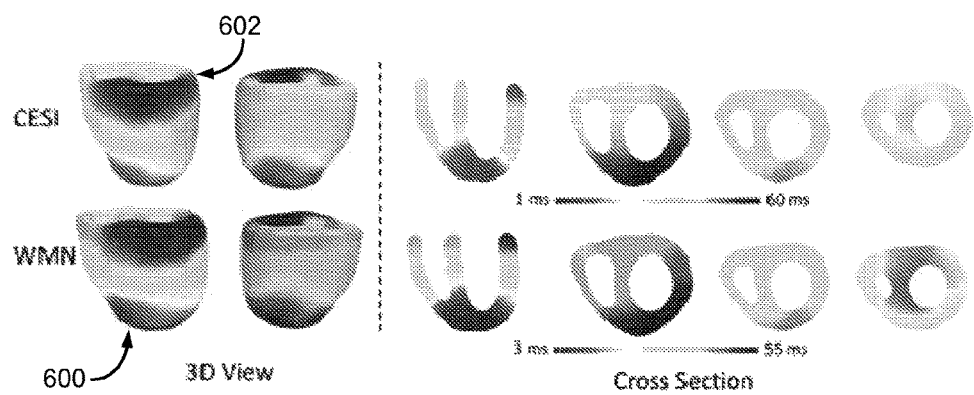
Figure 6C:
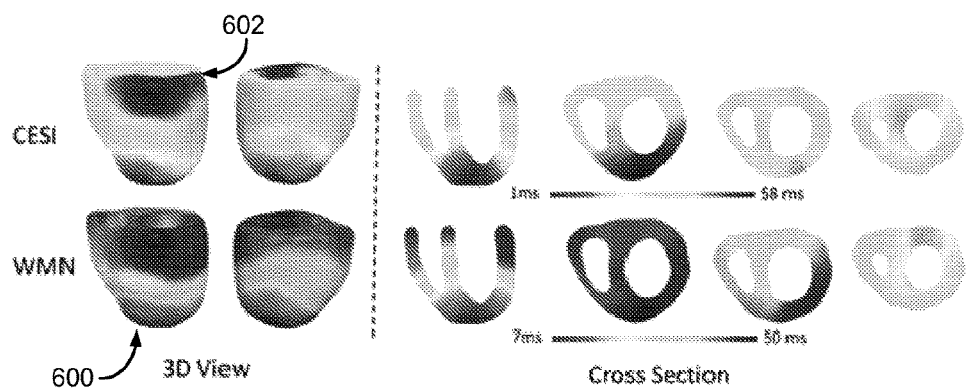
Figure 6D:
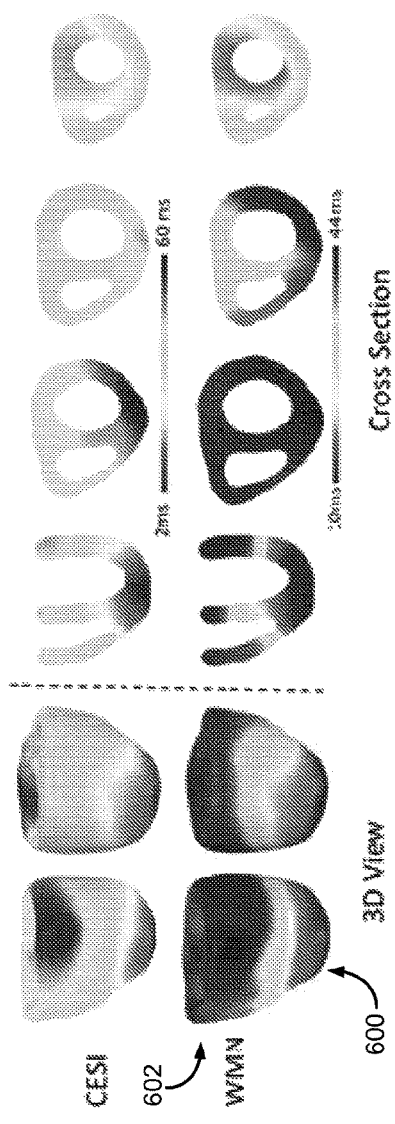
Figure 6E:
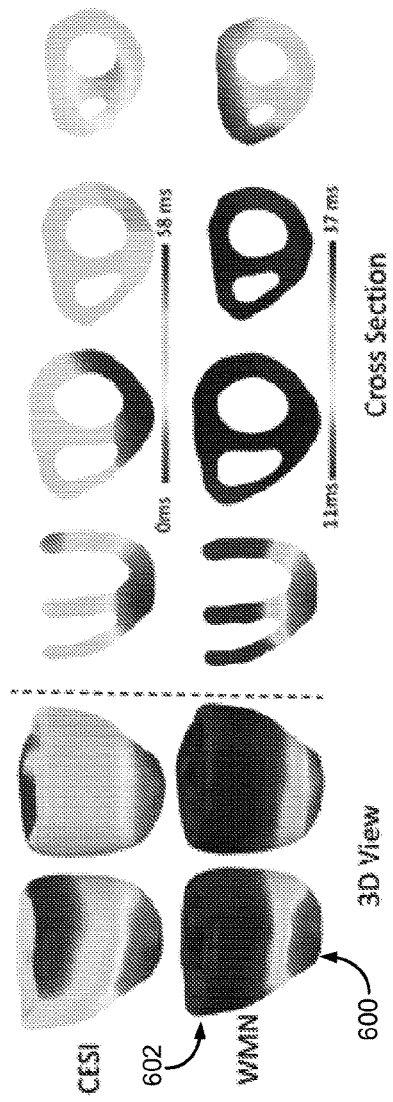

To evaluate the robustness of the CESI method, various modeling errors and co-registration errors were also simulated with 20 µV Gaussian white sensor noise. In FIGS. 6A-6E, examples of imaging results from a pacing simulation with various kinds of modeling and co-registration error are shown. All of the activation sequences are color coded from early activation 600 to late activation 602 as marked in color bars. FIG. 6A presents the computer simulated activation sequence. FIGS. 6B-6E display the imaging results and the comparisons of both CESI and WMN methods under various erroneous circumstances. FIG. 6B shows the results with torso geometry uncertainty where torso geometry is 10% dilated. FIG. 6C shows the results with heart position uncertainty where the whole myocardium is moved 4 mm towards the left lung. FIG. 6D shows a situation in which both errors in FIGS. 6B and 6C occur together. FIG. 6E shows the results with electrode-torso co-registration error where all of the electrodes are 10 mm upward.

Figure 7:
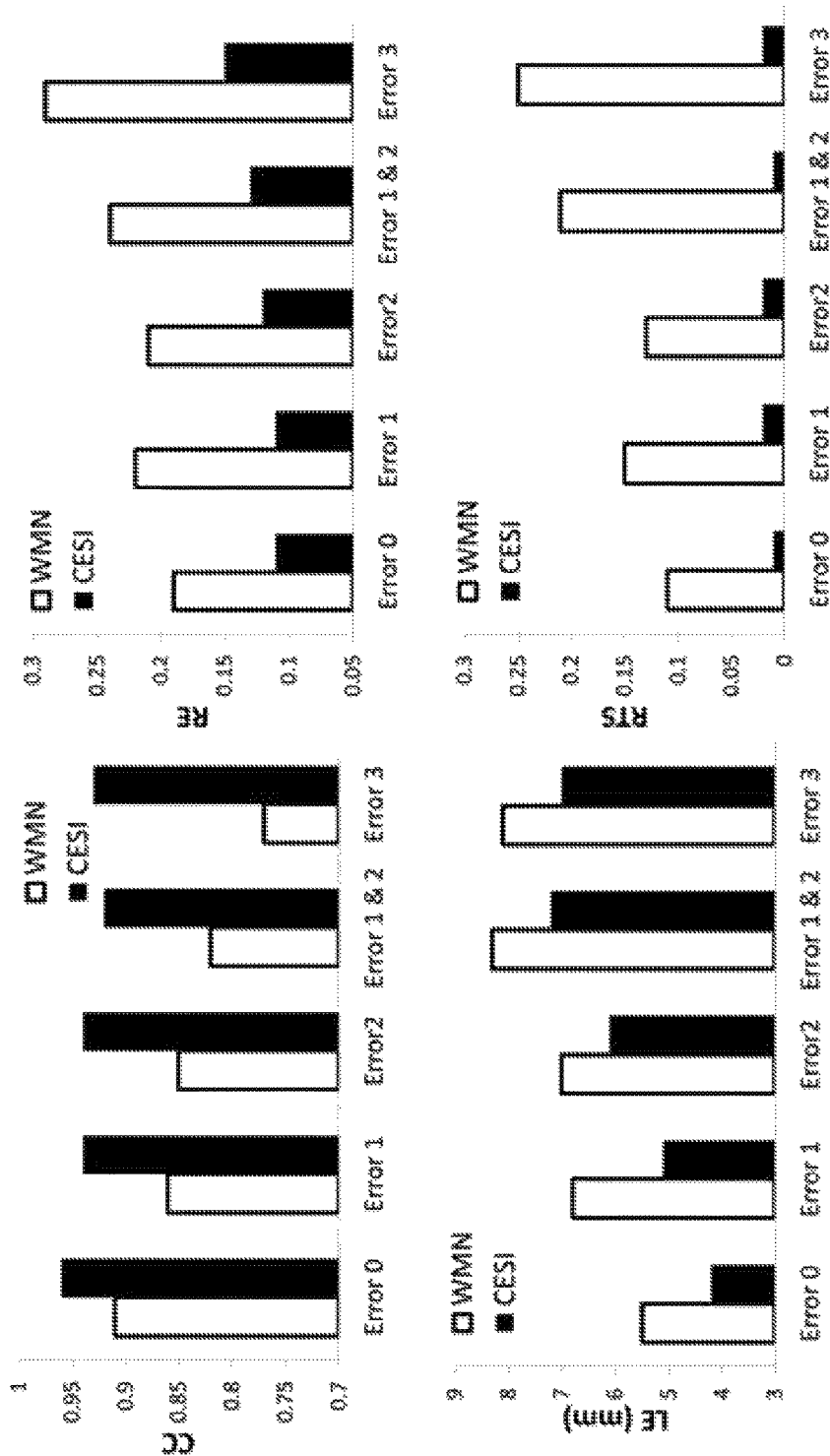
FIG. 7 is a set of graphs providing a comparison of the averaged statistics between the CESI method and the WMN method on single site pacing simulations with modeling errors on 12 single pacing sites.

The imaged results showed that the CESI method maintains the temporal resolution (shrinkage ~1 ms) and the activation pattern was barely affected by the modeling error or co-registration error. The CESI method maintains a stable overall pattern against modeling errors and little distortion was observed. The initiations of the beats are well localized by the CESI method with a clearly depicted early activation pattern. In FIGS. 6D, and 6E, where relatively heavy disturbance is imposed, the CESI method can still image the activation pattern with good accuracy. On the other hand, the WMN results, due to its physical constraints, are heavily distorted and losing details in activation pattern. In the early activation area in FIGS. 6B and 6D as well as the late activation in FIGS. 6D and 6E, the smearing effect is obvious due to the minimum-energy constraints that promote the smoothness. The statistics of the simulations are summarized in FIG. 7, where error 1 was torso geometry dilated 10%; error 2 was heart position moved 4 mm towards left lung; and error 3 was body surface electrodes move 10 mm towards right hand. Thus, the CESI method is much less affected by the modeling and co-registration error than the WMN method. CC, RE and RTS were maintained within a relatively small range under all those erroneous conditions while LE is increased due to the modeling and co-registration error but still lower than WMN.

B. Animal Results

Figure 8A:
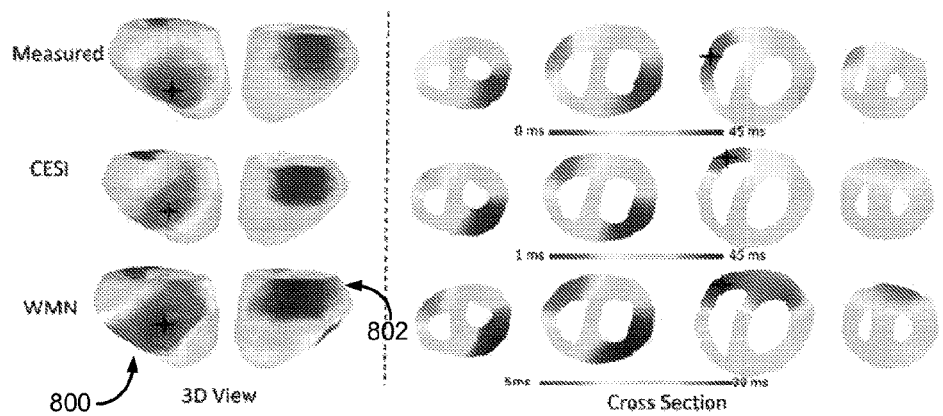
FIGS. 8A and 8B provide sets of graphs that compare examples and statistics between studies using the CESI method and the WMN method in rabbit pacing experiment.
Figure 8B:
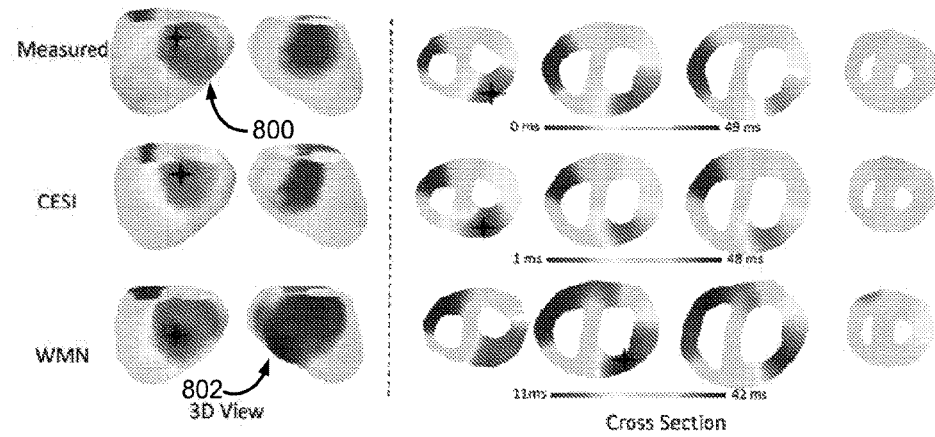
Figure 9:
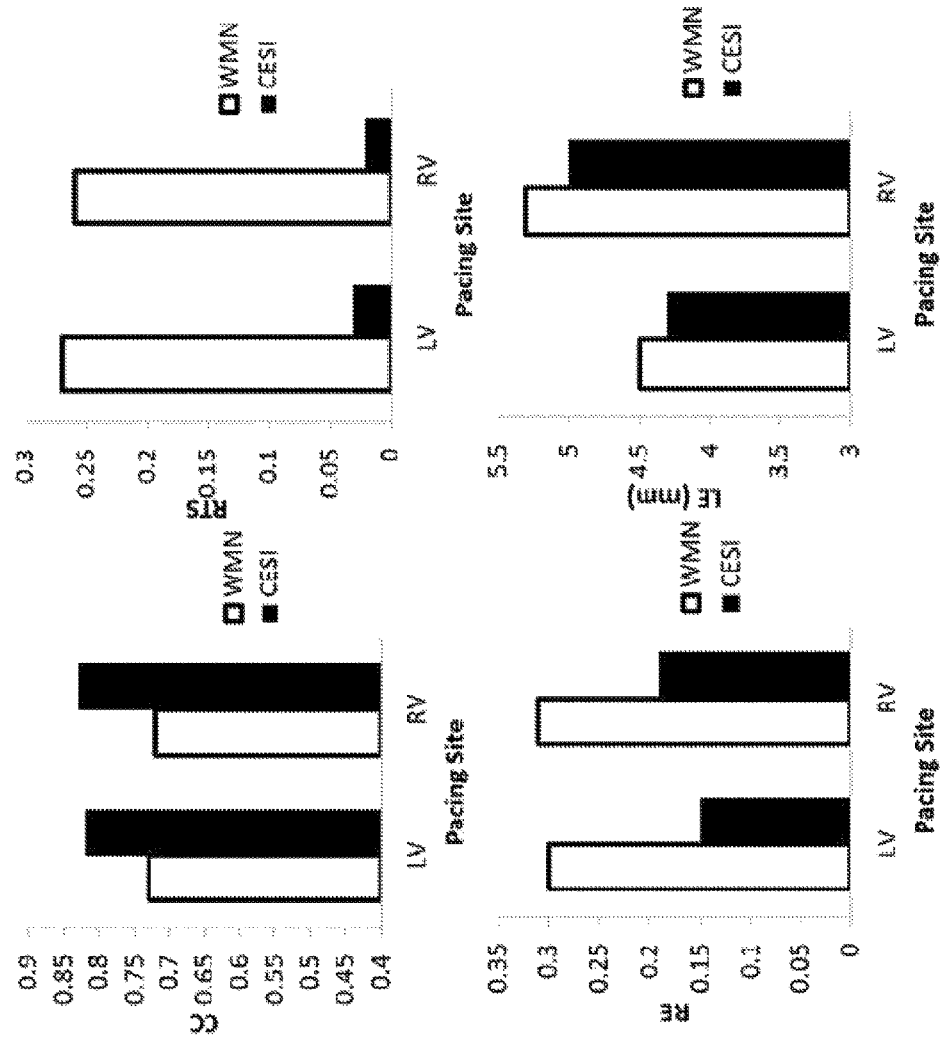
FIG. 9 is a set of graphs providing summarized statistics of activation imaging using the CESI method compared with the WMN method during pacing in rabbit.
Figure 10:
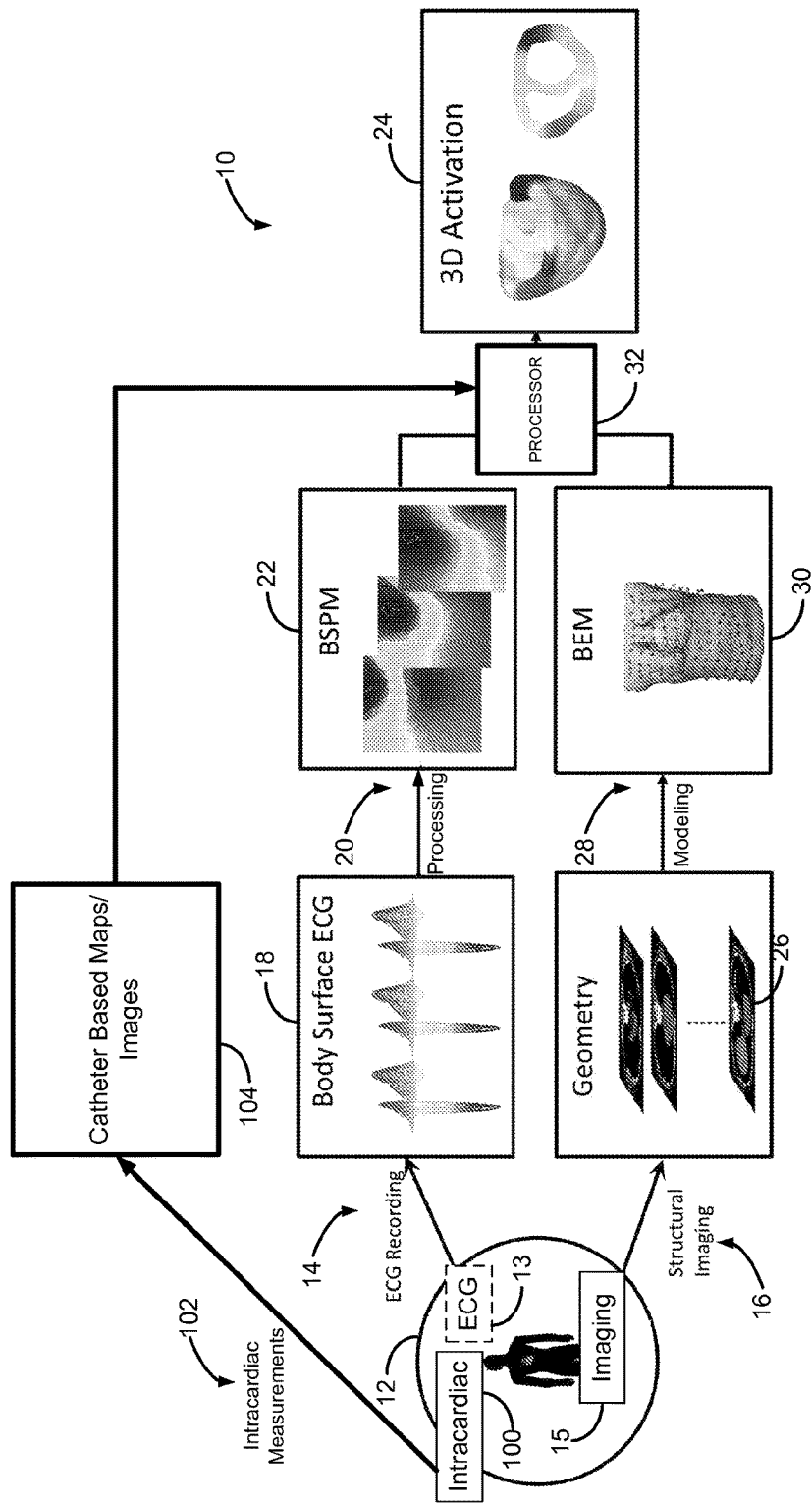
FIG. 10 is a schematic illustration of another system in accordance with the present invention.

Intra-cardiac transmural bipolar mapping has been established as an effective approach to measure the electrical activity and as a suitable approach to evaluate 3D cardiac imaging techniques. Referring to FIGS. 8A and 8B, 10 single pacing sites were employed in the pacing paradigm with simultaneous body surface and intra-cardiac mapping. Specifically, representative examples and statistics of the imaging results and comparisons are shown in FIGS. 8A and 8B. More particularly, FIGS. 8A and 8B present two imaging examples with single pacing at RV (8A) and LV (8B), respectively. The activation sequences are color-coded from early activation 800 to late activation 802. The black star represents the earliest activation site in both the imaged and measured activation maps. The focal pattern of the activation as well as its initiation has been well captured by the proposed method. The initiation is close to the pacing site and the early activation region is well focused and clear. The imaged activation that were acquired using the CESI method has good consistency with the measured results along the time course, from the early phase 600 to the end of the beat. The imaged results acquired using the CESI method, in comparison with those acquired using the WMN approach, are in higher temporal resolution with only little distortion especially in estimating the initial activation in the temporal domain. Statistics of quantitative evaluations and comparisons between CESI and WMN are summarized in FIG. 9. It can be observed that CC, RE, and LE are generally improved. The RTS acquired using the CESI method remains at 0.02, showing that the CESI approach is able to maintain high temporal resolution at experimental circumstances.

Therefore, a novel cardiac electrical imaging technique, referred to herein as cardiac electrical sparse imaging (CESI), has been invented and evaluated with computer simulations and animal experiments. CESI employs a novel 4D inverse problem formulation to exploit the temporal sparse property of cardiac electrical activity to preserve the temporal resolution and detailed activation information for improved accuracy and robustness. Computer simulations of both single and dual site pacing have shown that the CESI technique has the capability to image cardiac electrical activities with high spatiotemporal resolution and improved performance. CESI is able to image the activation sequence with higher CC and lower RE, LE, and RTS in comparison to conventional minimum norm based (WMN) methods, represented by WMN in the simulated pacing paradigms. In addition, imaging accuracy can be well maintained against various types of modeling error, indicating robustness in realistic clinical environments. Experiments in two rabbits using simultaneous BSPM and 3D intra-cardiac mapping further validated the CESI technique in a quantitative and realistic manner. Comparisons between CESI and WMN based imaging results show that the proposed method is able to outperform conventional minimum energy techniques both in theoretical and experimental evaluation. Results from both computer simulation and animal experiments show that the proposed CESI method is in good agreement with simulated activation sequence and experimentally measured cardiac activation.

Efforts have been made in pursuit for high resolution noninvasive imaging of cardiac electrical activity. The 4D inverse problem formulation in the CESI technique can image the whole cardiac electrical process and the weighted sparse constraints incorporate the temporal sparse property of cardiac electrical dynamics into reconstruction. In this invention a sparse problem formulation has been extended in a manner that is specifically designed and capable of imaging cardiac electrical activation with dipole based temporal weighted constraints and, thus, can reflect the electrophysiological dynamics. As explained above, the cardiac electrical activity can be approached as a sparse property. As explained herein, the temporal sparse property of cardiac electrical dynamics can be derived directly from electrophysiological knowledge of myocardial cellular depolarization. In the present invention, cellular cardiac electrophysiological property as guiding information is incorporated into the reconstructing mathematical framework of a physical model based 3D cardiac electrical imaging approach as temporal constraints. The property is based on a phenomenon that is not only observed in healthy but also in many pathological conditions. Moreover, this property is different from an electrophysiological model that requires certain individualized physiological knowledge which can vary as the condition changes. The inverse reconstruction of CESI employs a physical-model based strategy, but incorporates general physiological knowledge. The cardiac electrical inverse problem, by its nature, is often heavily ill-posed and thus not all the information can be directly reconstructed from the measurements. By incorporating the BSPM time course as input and temporal sparse constraints to pinpoint the activation time, CESI is able to greatly decrease the severity of ill-posedness and allow for a better representation of the information reflected in BSPM. The resolution of 1.5 mm spatially and 1 ms temporal can be achieved. Unlike the energy based physical constraints such as minimum norm and singular value truncation, sparse constrained solution attempts to not omit the detailed information in the solutions but to utilize the sparse property of the cardiac electrical activity for its reconstruction. With these constraints, the reconstruction algorithm will search for the solution that can fit the measurements well and at the same time has an electrophysiologically based sparse property that will help prevent the loss of detailed information. Also, as can be found in the problem formulation, CESI defines a constrained convex problem and has a unique solution that can be obtained equivalently with different optimization methods. The reconstruction strategy in CESI seeks for a balance between the physical model based techniques and their physiological model based counterparts. The experimental results described above demonstrate that CESI is capable of imaging the electrical activation in the myocardium more accurately and robustly than other methods, such as WMN, while at the same time working without any individual-based physiological information.

CESI incorporates raw data from various modalities to image the electrical activation in the 3D myocardium. In clinical practice, the quality of the raw data is limited. In the above-described results, various disturbances were simulated and tested with CESI. Compared to the simulated white noise, the hospital recorded noise allows to examine the performance of the imaging technique in a more realistic condition. The simulations with both generated white noise and hospital recorded sensor noise show that CESI was capable of imaging the electrical activation in the myocardium with higher accuracy than WMN methods. CESI was able to image with a CC=0.92, RE=0.15, LE=7 mm and RTS=0.02 under the white noise disturbance as strong as 80 µV. In the simulations utilizing the hospital recorded noise, CESI obtained a CC as high as 0.91, RE, LE and RTS were controlled as low as 0.16, 3.8 mm and 0.02, respectively. The results demonstrate that CESI is capable of producing stable and accurate imaging results in relatively realistic conditions. In addition to sensor noise, imaging results with various modeling errors that could occur in clinical conditions also demonstrate the robustness of CESI technique. Over the 4 kinds of modeling errors, the present method maintained a CC of 0.93, RE of 0.12, LE of 0.63 mm and RTS of 0.017, respectively. By comparing the modeling error results and the modeling error free statistics shown in FIG. 4, one can find that CESI has a strong robustness against the modeling errors and demonstrate the capability of functioning in complicated circumstances where the quality, and accuracy of raw data may be limited. For physical model based methods without physiological constraints, electrical energy distribution is heavily dependent by the accurate forward problem modeling, so with erroneous modeling the imaging accuracy will degenerate severely by the smearing and smoothing effect introduced. In contrast, the sparse constraints used in CESI provide an underlying propagation mechanism as additional information for imaging and therefore can prevent the activation sequence from server smoothing and distorting effects.

Rigorous evaluation in biological systems is crucial for the assessment of an imaging technique. Simultaneous recording of BSPM and intra-cardiac electrograms have been demonstrated as an effective approach to evaluate the performance of non-invasive imaging techniques in a realistic condition. The post-experiment CT scan can provide detailed information on the spatial location of intra-cardiac electrodes and therefore the electrical activity of the entire myocardium can be mapped over the 3D space. The results described above show that CESI can image the cardiac activation sequences in good concordance with the measured activation sequence via intracardiac mapping. The imaged activation initiation sites lie close to the measured initiation sites and the early activation area was clearly imaged. The animal experiment can evaluate the method in a condition that is similar to clinical practice but still have direct measurements on the electrical activity throughout the myocardial volume. As shown in FIG. 8, CESI can image the paced beat with good accuracy and localization of the initiation and therefore is expected to function with similar performance in realistic clinical conditions on focal arrhythmias. The comparisons between CESI and WMN show that the CESI imaged results suffer less distortion in activation time (averaged CC>0.8, RE<0.2, LE~5 mm) and can maintain temporal resolution (RTS<0.02). The animal experiment results demonstrate that CESI can be used to image the cardiac activation sequences in good concordance with intra-cardiac mapping.

In the clinical management of focal arrhythmias, such as premature ventricular complex and automatic ventricular tachycardia, catheter ablation is usually performed on the suspected initiations of the ectopic beats to terminate the arrhythmias. Therefore, the capability to correctly image the activation patterns in early phase of the ectopic beat is of clinical importance. As shown in FIGS. 5A-5D, the present method outperformed traditional minimum energy based method especially in early activation, identifying a clear initiation site and evading the smearing effect that the (weighted) minimum norm methods usually impose on the results and also leading a more accurate localization of ectopic initiations with error around 4 mm. The animal experiments, compared to computer simulation, demonstrate the potential clinical performance of CESI from a more realistic scope. Results show that CESI can localize the pacing sites, which can generate an ectopic pattern similar to focal arrhythmias, within 5 mm. Noting that this error is generated by an intrinsic reconstruction strategy, CESI can localize the ablation target within a smaller area and shorten the time of invasive mapping and ablation.

CESI promotes sparse electrical activities in the temporal domain in order to improve temporal resolution and accuracy of imaging. However, the method does not constrain the cardiac current density of "fire only once". The temporal sparse constraints seek to solve the inverse problem with the most zeros, while at the same time staying in good compliance with the residual term, which contains the information from BSPM. Therefore, multiple activation can coexist in the time course. The method is also compatible with non-focal arrhythmic activities, such as reentrant tachycardia.

As described, the above-detailed systems and methods may leverage information from non-interventional data acquisitions, such as ECG systems using surface electrodes to thereby create BSPMs. However, the above-described systems and methods may also use intracardiac electrophysiological recordings or interventional data acquisitions systems that include at least one electrode that interventionally positioned, generally, using a cardiac catheter. For example, systems and methods, such as described in U.S. Pat. No. 7,841,986, which is incorporated herein by reference in its entirety, may be used with the systems and methods of the present invention. For example, referring now to FIG. 10, the system described with respect to FIG. 1 may be adapted to incorporate an intracardiac monitoring system 100. In this case, the intracardiac monitoring system 100 may be used instead of the ECG system 13 and the use of ECG recordings 14 to produce body surface ECG data 18. Rather, the intracardiac monitoring system 100 can provide intracardiac measurements 102 that can be used create catheter based maps/images 104, as described in U.S. Pat. No. 7,841,986. The catheter based maps/images 104 can then be used by the processor 32 to create activation images 24. While the use of the intracardiac monitoring system 100 and catheter based maps/images may be an alternative to the ECG system 13 and the processing associated therewith, one may use both BSPM 22 and intracardiac catheter based maps/images 104 to perform cardiac activation imaging. The combination of both data sources may provide enhanced performance.

In conclusion, cardiac electrical sparse imaging (CESI) systems and methods are provided. These systems and methods have been evaluated with a series of computer simulations and animal pacing experiments. The simulation and animal results have demonstrated that CESI can image the cardiac electrical activation accurately and better than traditional linear inverse methods in various conditions and in a realistic experimental setup. The performance of CESI illustrates the ability to map cardiac electrical activity and aid catheter ablation of arrhythmia in a clinical setting.

All references included herein are incorporated herein by reference in their entirety. The present invention has been described in terms of one or more preferred embodiments, and it should be appreciated that many equivalents, alternatives, variations, and modifications, aside from those expressly stated, are possible and within the scope of the invention.

The invention claimed is:

1. A system for cardiac activation imaging, the system comprising:
    at least one data acquisition device configured to acquire data about an electrical activation of a heart of a subject; and
    a processor configured to receive the data acquired by the at least one data acquisition device and generate a cardiac electrical activation image by reconstructing an activation image of the heart of the subject using a weighted sparse constrained reconstruction weighted by a plurality of weights $W_{t,j}$ representing temporal weights of time instant t at location grid point j, wherein the reconstruction is sparse in a temporal domain.

2. The system of claim 1 wherein the temporal weighted sparse constrained reconstruction includes a dipole-wise temporal weighted sparse reconstruction applied as:

$$\hat{J}_T = \mathrm{argmin}\left(\left\|\vec{J}_T - L_T\vec{\Phi}_T\right\|_2^2\right) \text{ and}$$

$$\text{s.t.} \sum_t^T W_{t,i}\|\vec{J}_{t,i}\|_2^1 < \mu E_i \text{ for all } i;$$

where $L_T$ stands for a transfer matrix connecting the data over a period of time, $\Phi_T$, and an equivalent current density (ECD) $J_T$; $E_i$ represents estimated energy of ECD along time course t at location i; and $W_{i,j}$ and $E_i$ can be derived by:

$$W_{t,i} = \exp(-C_{t,i}/C_{max}) \text{ and } E_i = \sqrt{\sum_T C_{t,i}^2};$$

where $C_{i,j}$ is guiding information that can be solved with frame-by-frame minimum energy based inverse methods and μ is determined by a regularization algorithm.

3. The system of claim 1 wherein the processor is further configured to apply an image reconstruction framework that incorporates a cardiac electrophysiological property into a physical-model based cardiac electrical imaging approach as temporal constraints.

4. The system of claim 3 wherein the physical-model based cardiac electrical imaging approach is a three-dimensional (3D) physical-model based cardiac electrical imaging approach.

5. The system of claim 1 further comprising a display configured to provide the activation image in a color coding along a continuum from early activation to late activation.

6. The system of claim 1 wherein the processor is configured to receive body surface ECG time courses measured by body surface electrodes as an input and use the body surface ECG time courses as temporal sparse constraints in the temporal weighted sparse constrained reconstruction to identify cardiac activation sequence.

7. The system of claim 1 wherein the processor is configured to receive body surface MCG time courses measured by MCG sensors out of the body as an input and use the MCG time courses as temporal sparse constraints in the temporal weighted sparse constrained reconstruction to identify cardiac activation sequence.

8. The system of claim 1 wherein the processor is configured to balance fit with the data acquired and loss of detailed information.

9. The system of claim 8 wherein the temporal weighted sparse constrained reconstruction includes an electrophysiologically based sparse property that protects against loss of detailed information from the data acquired.

10. The system of claim 9 wherein the electrophysiologically based sparse property is a temporal sparse property of cardiac electrical dynamics derived directly from electrophysiological knowledge of myocardial cellular depolarization.

11. The system of claim 1 wherein the at least one data acquisition device includes one of an electrocardiography (ECG) device or an interventional cardiac monitoring device such as a cardiac catheter.

12. A method for cardiac activation imaging, the method comprising:
acquiring data about an electrical activation of a heart of a subject using at least one sensor;
reconstructing an activation image of the heart of the subject using the acquired data and a weighted sparse constrained reconstruction weighted by a plurality of weights $W_{t,i}$ representing temporal weights of time instant t at location grid point i, wherein the reconstruction is sparse in a temporal domain; and
displaying the activation image of the heart.

13. The method of claim 12 wherein the temporal weighted sparse reconstruction is applied as:

$$\hat{J}_T = \mathrm{argmin}\left(\left\|\vec{J}_T - L_T \vec{\Phi}_T\right\|_2^2\right) \text{ and}$$

$$\mathrm{s.t.} \sum_t^T W_{t,i} \left\|\vec{J}_{t,i}\right\|_2^1 < \mu E_i \text{ for all } i;$$

where $L_T$ stands for a transfer matrix connecting the data over a period of time, $\Phi_T$, and an equivalent current density (ECD) $J_T$; $W_{t,i}$ represents temporal weights of time instant t at location grid point i; $E_i$ represents estimated energy of ECD along time course t at location i; and $W_{i,j}$ and $E_i$ can be derived by $$W_{t,i} = \exp(-C_{t,i}/C_{max}) \text{ and } E_i = \sqrt{\sum_T C_{t,i}^2};$$

where $C_{i,j}$ is guiding information that can be solved with frame-by-frame minimum energy based inverse methods and μ is determined by a regularization algorithm.

14. The method of claim 12 wherein the temporal weighted sparse constrained reconstruction applies an image reconstruction framework that incorporates a cardiac electrophysiological property into a physical-model based cardiac electrical imaging approach as temporal constraints.

15. The method of claim 14 wherein the cardiac electrophysiological property is a temporal sparse property of cardiac electrical dynamics derived directly from electrophysiological knowledge of myocardial cellular depolarization.

16. The method of claim 14 wherein the physical-model based cardiac electrical imaging approach is a three-dimensional (3D) physical-model based cardiac electrical imaging approach.

17. The method of claim 12 further comprising receiving body surface ECG time course data measured by body surface electrodes and using the body surface ECG time course data as temporal sparse constraints in the temporal weighted sparse constrained reconstruction to identify cardiac activation time.

18. The method of claim 12 further comprising receiving MCG time course data measured by MCG sensors and using the MCG time course data as temporal sparse constraints in the temporal weighted sparse constrained reconstruction to identify cardiac activation time.

19. The method of claim 12 wherein the temporal weighted sparse constrained reconstruction includes an electrophysiologically based sparse property that protects against loss of detailed information from the acquired data.

20. The method of claim 19 wherein the electrophysiologically based sparse property is a temporal sparse property of cardiac electrical dynamics derived directly from electrophysiological knowledge of myocardial cellular depolarization.

21. The method of claim 12 wherein the acquired data includes at least one an electrocardiography (ECG) acquired using surface electrodes or an interventional electrode such as a cardiac catheter.

22. The method of claim 12 wherein reconstructing includes defining a constrained convex problem that has a unique solution.

* * * * *

UNITED STATES PATENT AND TRADEMARK OFFICE
CERTIFICATE OF CORRECTION

PATENT NO. : 10,098,557 B2
APPLICATION NO. : 15/036961
DATED : October 16, 2018
INVENTOR(S) : Bin He et al.

It is certified that error appears in the above-identified patent and that said Letters Patent is hereby corrected as shown below:

In the Specification

Column 7, Line 42, "$C_{max}$" should be --$C_{max,i}$--.

Signed and Sealed this
Fourth Day of December, 2018

Andrei Iancu
*Director of the United States Patent and Trademark Office*